United States Patent [19]

Harvey et al.

[11] Patent Number: 5,674,753
[45] Date of Patent: *Oct. 7, 1997

[54] EPIDERMAL GROWTH FACTOR RECEPTOR ECTODOMAIN

[75] Inventors: Jeanne P. Harvey, Oakland; Victoria A. Crebbin, Alameda; Roger P. Walker, Benicia; Victor Liu, Fremont; Susan L. Hammond, Alameda, all of Calif.; Patricia A. McDonald, Durham, N.C.

[73] Assignee: Chiron Diagnostics Corporation, Medfield, Mass.

[*] Notice: The term of this patent shall not extend beyond the expiration date of Pat. No. 5,344,760.

[21] Appl. No.: 288,481

[22] Filed: Aug. 10, 1994

Related U.S. Application Data

[63] Continuation of Ser. No. 889,718, May 27, 1992, Pat. No. 5,344,760, which is a continuation-in-part of Ser. No. 709,503, Jun. 3, 1991, abandoned.

[51] Int. Cl.$^6$ ................................................. G01N 33/566
[52] U.S. Cl. ....................................... 436/501; 436/822
[58] Field of Search ............................ 435/7.1, 7.23; 530/387.7, 250; 514/2; 436/507

[56] References Cited

U.S. PATENT DOCUMENTS

| | | | |
|---|---|---|---|
| 4,699,877 | 10/1987 | Cline et al. | 435/6 |
| 4,933,294 | 6/1990 | Waterfield et al. | 436/501 |
| 4,943,533 | 7/1990 | Mendelsohn et al. | 435/240.27 |
| 5,221,612 | 6/1993 | Zhau et al. | 435/7.92 |

FOREIGN PATENT DOCUMENTS

| | | |
|---|---|---|
| 2026250 | 3/1991 | Canada . |
| 214520 | 3/1987 | European Pat. Off. . |
| 8503357 | 8/1985 | WIPO . |
| 9111715 | 8/1991 | WIPO . |

OTHER PUBLICATIONS

Di Fiora et al., *Cell* 51:1063–1070, 24 Dec. 1987.
Adamson and Rees, "Epidermal growth factor receptors", *Molecular and Cellular Biochemistry*, 34: 129–152 (1981).
Brauknect et al., "Occurrence of Epidermal Growth Factor Receptors in Human Adnexal Tumors and Their Prognostic Value in Advanced Ovarian Carcinomas", *Gynecologic Oncology*, 29: 147–157 (1988).
Berger et al., "Epidermal Growth Factor Receptors in Lung Tumours", *Journal of Pathology*, 152: 297–307 (1987).
Carlin and Knowles, "Identity of human epidermal growth factor (EGF) receptor with glycoprotein SA–7: Evidence for differential phosphorylation of the two components of the EGF receptor from A31 cells", *PNAS* (USA), 79: 5026–6030 (Aug. 1982).
Cohen et al., "A Native 170,000 Epidermal Growth Factor Receptor–Kinase Complex from Shed Plasma Membrane Vesicles", *Journal of Biological Chemistry*, 257(3): 1523–1531 (Feb. 19, 1982).

Cooper et al., "Epidermal Growth Factor Receptor Metabolism and Protein Kinase Activity in Human A431 Cells Infected with Snyder–Theilen Feline Sarcoma Virus or Harvey or Kirsten Murine Sarcoma Virus", *Journal of Virology*, 48: 752–764 (Dec. 1983).
Downward et al., "Close similarity of epidermal growth factor receptor and v–erbB oncogene protein sequences", *Nature*, 307(5951): 521–527 (1984).
Fabricant et al., "Nerve growth factor receptors on human melanoma cells in culture", *PNAS* (USA) 74(2): 565–569 (Feb. 1977).
Fitzpatrick et al., "Epidermal Growth Factor Binding by Breast Tumor Biopsies and Relationship to Estrogen Receptor and Progestin Receptor Levels", *Cancer Research*, 44: 3348–3453 (Aug. 1984).
Grimaux et al., "A Simplified Immuno–Enzymetric Assay of the Epidermal Growth Factor Receptor in Breast Tumors: Evaluation in 282 Cases", *Int. J. Cancer*: 45: 255–262 (1990).
Gullick et al., "A Radioimmunoassay for Human Epidermal Growth Factor Receptor", *Analytical Biochemistry*, 141: 253–261 (1984).
Gullick et al., "The structure and function of the epidermal growth factor receptor studied by using antisynthetic peptide antibodies", *Proc. R. Soc. Lond.*, B226: 127–134 (1985).
Gullick et al., "Expression of Epidermal Growth Factor Receptors on Human Cervical, Ovarian and Vulval Carcinomas", *Cancer Research*, 46: 285–292 (Jan. 1986).
Gullick and Waterfield, "Epidermal growth factor and its receptor", Chapter 1, pp. 15–34 in Ellis Horward Series In Biomedicine: *The Molecular Biology of Receptors. Techniques and Applications of Receptor Research* (Stresberg ed.) (VCH Publishers Inc. NY, NY 1987).
Hapgood et al., "Monoclonal antibodies against epidermal growth factor receptor induce prolactin synthesis in cultured rat pituitary cells (GH$_3$)", *PNAS* (USA), 80: 6451–6455 (Nov. 1983).
Hendler and Ozanne, "Human Squamous Cell Lung Cancers Express Increased Epidermal Growth Factor Receptors", J. Clin. Inves., 74: 647–651 (1984).

(List continued on next page.)

*Primary Examiner*—John Ulm
*Attorney, Agent, or Firm*—Leona L. Lauder; Arthur S. Morgenstern

[57] ABSTRACT

Diagnostic/prognostic methods are provided for detecting and/or quantitating in the body fluids, preferably serum, of mammals carrying a malignant tumor burden, elevated levels of a portion of the epidermal growth factor receptor (EGFr) which comprises substantially the EGFr ectodomain having a molecular weight in the range of from about 90 kilodaltons (kd) to about 115 kd, preferably from about 95 kd to about 105 kd, and more preferably about 100 kd. Substantially pure compositions comprising EGFr ectodoman protein and/or fragments thereof are disclosed as well as test kits for performing the disclosed assays.

18 Claims, No Drawings

OTHER PUBLICATIONS

Humphrey et al., "Amplification and Expression of the Epidermal Growth Factor Receptor Gene in Human Glioma Xenografts", *Cancer Research, 48:* 2231–2238 (Apr. 15, 1988).

Humphrey et al., "Anti–synthetic peptide antibody reacting at the fusion junction of deletion–mutant epidermal growth factor receptors in human glioblastoma", *PNAS* (USA), 87: 4207–4211 (Jun. 1990).

Kawawato et al., "Growth stimulation of A431 cells by epidermal growth factor: Identification of high–affinity receptors for epidermal growth factor by an anti–receptor monoclonal antibody", PNAS (USA), 80: 1337–1341 (Mar. 1983).

Libermann et al., "Expression of Epidermal Growth Factor Receptors in Human Brain Tumors", *Cancer Research, 44:* 753–760 (Feb. 1984).

Lin et al., "Expression Cloning of Human EGF Receptor Complementary DNA: Gene Amplification and Three Related Messenger RNA Products in A431 Cells", *Science, 224:* 843–847 (May 25, 1994).

Malden et al., "Selective Amplification of the Cytoplasmic Domain of the Epidermal Growth Factor Receptor Gene in Glioblastoma Multiforme", *Cancer Research, 48:* 2711–2714 (May 15, 1988).

Mayes and Waterfield, "Biosynthesis of the epidermal growth factor receptor in A431 cells", *EMBO, J., 3:* 531–537 (1984).

Merlino et al., "Amplification and Enhanced Expression of the Epidermal Growth Factor Receptor Gene in A431 Human Carcinoma Cells", *Science, 229:* 417–419 (Apr. 27, 1984).

Neal et al. "Epidermal–Growth–Factor Receptors in Human Bladder Cancer: Comparison of Invasive and Superficial Tumours", *Lancet, 1*(8425): 366–368 (Feb. 16, 1985).

Nicholson et al., "Quantitative Assays of Epidermal Growth Factor Receptor in Human Breast Cancer: Cut–off Points of Clinical Relevance", *Int. J. Cancer, 42:* 36–41 (1988).

Nicholson et al., "Expression of Epidermal Growth Factor Receptors Associated with Lack of Response to Endocrine Therapy in Recurrent Breast Cancer", *Lancet. 1*(8631): 182–185 (Jan. 28, 1989).

Parker et al., "Monoclonal Antibodies against the Human Epidermal Growth Factor Receptor from A431 Cells", *Journal of Biological Chemistry,* 259(15): 9906–9912 (Aug. 10, 1984).

Perez, et al., "Epidermal growth factor receptors in human breast Cancer", *Breast Cancer Research Treatment, 4:* 189–193 (1984).

Petch et al., "A Truncated, Secreted Form of the Epidermal Growth Factor Receptor Is Encoded by an Alternatively Spliced Transcript in Normal Rat Tissue", *Molecular and Cellular Biology,* 10(6): 2973–2982 (Jun. 1990).

Richert et al., "Epidermal Growth Factor Receptor", *Journal of Biological Chemistry, 258:* 8902–8907 (1983).

Sainsbury et al., "Epidermal–Growth–Factor Receptor Status as Predicator of Early Recurrence of the Death from Breast Cancer", Lancet, 1(8547): 1398–1402 (Jun. 20, 1987).

Sohreiber et al., "Monoclonal antibodies against receptor for epidermal growth factor induce early and delayed effects of epidermal groth factor", *PNAS* (USA), 78(12): 7535–7539 (Dec. 1981).

Smith et al., "Characterization and Quantitation of the Epidermal Growth Factor Receptor in Invasive and Superficial Bladder Tumors", *Cancer Research, 49:* 5810–5815 (1989).

Stoscheck and Carpenter, "Down Regulation of Epidermal Growth Factor Receptors: Direct Demonstration of Receptor Degradation in Human Fibroblasts", *Journal of Cell Biology, 98:* 1048–1053 (Mar. 1984).

Thompson and Gill, "The EGF receptor: structure, regulation and potential role in malignancy", *Cancer Surveys,* 4(4): 767–788 (1985).

Ullrich et al., "Human epidermal growth factor receptor cDNA sequence and aberrant expression of the amplified gene in A431 epidermoid carcinoma cells", *Nature, 309* (5967): 418–425 (May 31, 1984).

Waterfield et al., "Anti Epidermal Growth Factor Receptor Monoclonal Antibodies", *Cell Biology International Reports,* 7(7): 535–537 (Jul. 1983).

Waterfield et al., "Anti–epidermal–growth–factor receptor monoclonal antibodies", *Chemical Abstracts, 99*(19): 156453e (p. 455) (Nov. 7, 1983).

Waterfield, et al., "A Monoclonal Antibody to the Human Epidermal Growth Factor Receptor", *Journal of Cellular Biochemistry,* 20: 149–161 (1982).

Weber et al., "Production of an Epidermal Growth Factor Receptor–Related Protein", Science, 224: 294–297 (Apr. 20, 1984).

Weber, "Truncated EGF receptor: functional aspects of its secretion", *Acta Endocrino Logica, 177* (Suppl. 287): 47 (No. 55) 1988).

Wrann and Fox, "Identification of Epidermal Growth Factor Receptors in a Hyperproducing Human Epidermoid Carcinoma Cell Line", *Journal of Biological Chemistry, 254*(17): 8083–8086 (Sep. 10, 1979).

Xu et al., "Human epidermal growth factor receptor cDNA is homologous to a variety of RNAs overproduced in A431 carcinoma cells", *Nature, 309*(5971): 806–810 (Jun. 1984).

Xu et al., "Characterization of epidermal growth factor receptor gene expression in malignant and normal human cell lines", *PNAS* (USA), 81: 7308–7312 (Dec. 19, 1984).

EPIDERMAL GROWTH FACTOR RECEPTOR ECTODOMAIN

RELATED APPLICATION

This application is a continuation of U.S. Ser. No. 07/889,718, filed May 27, 1992, now U.S. Pat. No. 5,344,760, which in turn, is a continuation-in-part of now abandoned U.S. Ser. No. 07/709,503, filed Jun. 3, 1991. Priority is claimed from both of said prior filed applications.

FIELD OF THE INVENTION

This invention is in the medical arts; more specifically, it is in the area of diagnostics/prognostics; and still more specifically, it is in the fields of oncology and immunochemistry. This invention relates to the epidermal growth factor receptor (EGFr) and assays designed to detect and/or quantitate in the body fluids of mammals a portion of said receptor, which comprises substantially the ectodomain of EGFr and has a molecular weight in the range of from about 90 kilodaltons (kd) to about 115 kd, preferably from about 95 kd to about 105 kd, and still more preferably about 100 kd.

BACKGROUND OF THE INVENTION

The mechanism for malignancy of mammalian cells has been and continues to be the subject of intense investigation. One of the most promising areas is the elucidation of how oncogenes are turned on and turned off.

Oncogenes were first detected in retroviruses, and then cellular counterparts of the viral oncogenes were found. A score of oncogenes has been isolated since the early 1970's from retroviruses that variously cause carcinoma, sarcoma, leukemia or lymphoma in chickens, other birds, rats, mice, cats or monkeys. In each case, the oncogene has been found to be closely related to a normal gene in the host animal and to encode an oncogenic protein similar to a normal protein. The proteins encoded by oncogenes function abnormally and seem to play a part in ordaining the transformation of a normal cell into a cancer cell. Genes in the DNA of various kinds of tumor cells, when introduced by transfection into normal cultured cells, transform the normal cells into cancer cells.

The oncogenes are virtual or almost virtual copies of proto-oncogenes. Whatever the specific mechanism that converts a proto-oncogene into an oncogene may be, an oncogene exerts its effect by means of the protein it encodes. The products of the proto-oncogenes appear to have roles that are critical in the regulation of cell growth and differentiation and in embryonic development. Transforming proteins may have their profound effects on cells because they disturb these fundamental cellular processes.

Enzymatic activity in catalyzing the addition of a phosphate molecule to an amino acid (phosphorylation) is known to be important in the control of protein function. The enzymes that phosphorylate proteins are called protein kinases (from the Greek kinein, "to move"). Almost one-third of all the known oncogenes code for protein kinases specific for tyrosine residues.

Epidermal growth factor (EGF), when added to a culture of individual cells, stimulate the cells to divide. EGF in vitro can trigger a variety of morphological and biochemical changes that resemble those characteristic of transformed cells, and has also been implicated in the abnormal regulation of proliferation shown by transformed and tumor-derived cell lines. Epidermal growth factor (EGF) promotes the growth of many cell types in vitro and inhibits proliferation of several cell types, for example, A431 epidermoid carcinoma cells and certain human breast cancer cells [Kawamoto et al., PNAS (USA), 80: 1337–1341 at p. 1337 (March 1983)].

EGF delivers its signals by binding to specific protein receptors embedded in the cell's plasma membrane. When the receptor protein for EGF was isolated, it was found to be associated with tyrosine kinase activity, which is stimulated when an EGF molecule binds to the receptor.

The receptor protein for EGF, the epidermal growth factor receptor (EGFr), is a 170 kilodalton (kd) transmembrane glycoprotein which comprises a cytoplasmic or tyrosine kinase domain, a transmembrane region and an extracellular domain or ectodomain which contains the binding site for epidermal growth factor (EGF) and transforming growth factor alpha (TGF-α) [Marquardt and Todaro, J. Biol. Chem., 257: 5220–5225 (1982); Carpenter et al., PNAS (USA) 80: 5627–5630 (1983)]. The cytoplasmic domain comprises 542 amino acids (C-terminal residues), and the ectodomain comprises 621 amino acids (N-terminal residues); they are linked by a short transmembrane region of about 23 amino acids [Ullrich et al., Nature, 309 (5967): 418–425 (May 31, 1984); Gullick et al., Proc. R. Soc. Lond., B 226: 127–134 (1985)].

EGFr is a cell membrane macromolecule that is widely distributed in cells derived from all three embryonic germ layers. The wide distribution of the receptor in cells and tissues indicates that EGF may have an important role to play in growth control. Many normal cells express 10–100,000 EGFrs [Adamson and Rees, Mol. Cell Biochem., 34: 129–152 (1981); however, increased numbers of EGFrs are present in several types of human tumors, including gliomas and meningiomas, squamous carcinoma of the lungs, and ovarian, cervical and renal carcinomas [Thompson and Gill, Cancer Surveys, 4(4): 768–788 (1985]. The human epidermoid carcinoma cell line A431 expresses about 10- to 50-fold more receptors than the majority of other cells [Fabricant et al., PNAS (USA), 74(2): 565–569 (1977); Wrann and Fox, J. Biol. Chem., 254: 8083–8086 (1979)].

The gene that encodes the EGFr is related to the avian erythroblastosis virus (AEV) oncogene which encodes the v-erb-B transforming protein. The v-erb-B oncogene is highly homologous with the EGFr transmembrane and tyrosine kinase domains; however, the v-erb-B oncogene does not encode the extracellular ligand-binding domain or a short C-terminal region which contains the main sites of self-phosphorylation [Downward et al., Nature, 307: 521–527 (1984)].

EGFr has also been shown to have a high degree of structural and sequence homology with the c-erbB-2 protein encoded by the c-erbB-2 oncogene. As is the EGFr, the c-erbB-2 protein is a transmembrane glycoprotein that has an extracellular domain, a transmembrane domain that includes two cysteine-rich repeat clusters, and a cytoplasmic kinase domain. However, the c-erbB-2 protein has a molecular weight of 185 kd and an unidentified ligand [Semba et al., PNAS, 82: 6497–6501 (1985)]. The EGFr and c-erbB-2 protein are encoded by different genes.

Ligand binding to the EGFr is one factor involved in the control of cellular proliferation. Binding of EGF to the ectodomain of EGFr results in a cascade of events beginning with the autophosphorylation of the receptor, followed by aggregation and internalization of EGFrs and ultimately cellular proliferation. It has been demonstrated that ligand binding to the EGFr promotes phosphorylation of the c-erbB-2 protein [King et al., *EMBO J.*, 7 (6): 1647–1651 (1988)]; that observation suggests a mechanism for communication between receptors that could affect control of cell growth. Overexpression of EGFrs, as occurs in A431 cells, can augment cell growth because of increased formation of active ligand/receptor complexes.

Cellular proliferation exhibited by transformed cells may be due to an autocrine mechanism wherein transformed cells both secrete mitogenic growth factors and respond to them in an uncontrolled fashion [Sporn and Todaro, *N. Engl. J. Med.*, 303: 878–880 (1980)]. Thus, the expression levels of growth factors and their receptors are considered important factors in the control of growth.

Gene amplification has been demonstrated to be one mechanism for aberrant EGFr expression in A431 cells and in some glioblastoma multiforms tumors but not in all human tumors [Thompson and Gill, *Cancer Surveys*, 4(4): 768–788 (1985)]. Studies with tumor cell lines in vitro have shown a direct relationship between the levels of activated EGFr and cellular proliferation. Further, the growth rate of tumors in nude mice was shown to be directly related to the EGFr levels, that is, the most rapidly growing tumors displayed elevated EGFr levels [Thompson and Gill, id.]. Therefore, evidence indicates that measurement of EGFr levels could be important in cancer management.

EGF receptors (EGFrs) can be detected in a variety of cells either by measurement of EGF binding [reviewed in Adamson and Rees, *Mol. Cell Biochem.*, 34:129–152 (1981) ], by cross-linking of labeled EGF to its receptor [reviewed in Linsley et al., in *Membrane Receptors* (eds. Jacobs and Cuatrecasas), vol. B11: 87–113 (Chapman J. Hall, London and New York 1981)], or through the use of monoclonal antibodies [Schreiber et al., *PNAS* (USA), 78: 7535–7539 (1981); Waterfield et al., *J. Cell Biochem.*, 20: 149–161 (1982); Kawamoto et al., *PNAS* (USA), 80: 1337–1341 (1983); Richert et al., *J. Biol. Chem.*, 258: 8902–8907 (1983); Gregoriou and Rees, *Cell Biol. Int. Reports*, 7: 539–540 (1983); and Schlessinger et al., in *Receptors and recognition: antibodies against receptors* (ed. Greaves) (Chapman and Hall, London, 1985)].

Several groups have investigated the expression of EGFr in a variety of tumors using quantitative as well as semi-quantitative immunohistochemical methods. The types of tumors investigated include gynecological [Bauknecht et al., *Gynecologic Oncology*, 29(2): 147–157 (February 1988); Gullick et al., *Cancer Res.*, 46: 285–292 (1986)]; lung [Berger et al., *J. Pathol.*, 152: 297–307 (1987)]; bladder [Smith et al., *Cancer Res.*, 49: 5810–5815 (1989); Neal et al., *Lancet*, 366–368 (1985)]; and breast carcinomas [Fitzpatrick et al., *Cancer Res.*, 44: 3448–3453 (1984); Nicholson et al., *Int. J. Cancer*, 42: 36–41 (1988); and Nicholson et al., *Lancet*, 182–185 (1989)]. Such studies almost exclusively rely upon radioligand binding methodology for quantitating EGFr in tissue samples.

The most extensive correlations of EGFr expression with clinical data have been carried out in studies with breast cancer patients [Nicholson et al., *Int. J. Cancer*, 42: 36–41 (1988); Sainsbury et.al., *Lancet*, 1398–1402 (1987)]. In several studies with up to 246 patients, it was demonstrated that EGFr is a highly significant marker of poor prognosis for breast cancer [Sainsbury et al., id.]. It is considered to be the most important variable in predicting relapse-free and overall survival in lymph node-negative patients, and to be the second most important variable, after nodal status, in lymph node-positive patients. In general, EGFr positive tumors are larger and occur in a higher proportion of patients with lymph node involvement.

Further, in breast cancer studies, EGFr has been determined to be as good an indicator as the estrogen receptor (ER) in predicting the response to endocrine therapy [Nicholson et al., *Lancet*, 182–185 (1989)]. Many ER positive patients don't respond to endocrine therapy, whereas a small percentage of ER negative patients do respond. EGFr positive tumors do not respond to endocrine therapy upon relapse, regardless of ER status, and EGFr positivity reduces the response rate even in ER positive tumors.

Studies have demonstrated a survival advantage for women that have ER positive tumors; most of such tumors are EGFr negative. ER negative tumors are divided into EGFr positive and negative groups, wherein the ER negative/EGFr positive group have a poor prognosis, and the ER negative/EGFr negative group have as good a relapse-free survival rate as the ER positive group. Thus, the measurement of EGFr levels is a useful adjunct to ER level measurement in breast cancer management.

Ovarian, cervical, vulval and endometrial tumors also overexpress EGFr. An association between EGFr levels and prognosis similar to that for breast cancer has been shown for endometrial cancer; however, increased EGFr levels associated with ovarian cancer correlate with a high response rate to chemotherapy [Bauknecht et al., supra]. EGFr expression and gene amplification has been more frequently observed among squamous cell carcinomas of the cervix and lung than in other types of cancer; however, correlation with tumor aggressiveness in such cancers has not been proven [Gullick et al., supra]. Quantitative studies with bladder tumors have shown that elevated EGFr levels are indicative of the most invasive tumors [Smith et al., supra; Neal et all, supra].

Waterfield et al., *Cell Biol. Internat'l Reports*, 7 (7):535–537 (July 1983), reported the generation of a series of monoclonal antibodies raised against the human cervical carcinoma cell line A431. Hapgood et al., *PNAS* (USA), 80 (21):6451–6455 (November 1983), describes the generation of different monoclonal antibodies against various domains of the EGFr. A IgM monoclonal is reported to bind to a domain close to the combining site for EGF, and another IgG monoclonal antibody is described as binding to an antigenic determinant that is remote from the combining site for EGF (p. 6454, lines 16–23).

Ullrich et al., *Nature*, 309 (5967):418–425 (May 31, 1984), provides the complete 1,210 amino acid sequence of the EGFr precursor deduced from cDNA clones derived from placental and A431 carcinoma cells. The receptor gene is therein noted to be amplified and rearranged in A431 cells, generating a truncated 2.8-kilobase (kb) mRNA which encodes only the extracellular EGFr binding domain. [See also, Merlino, *Science*, 229: 417–419 (Apr. 27, 1984); Xu et al., *Nature*, 309: 806–810 (Jun. 18, 1984); and Lin et al., *Science*, 224: 843–848 (1984)]. Ullrich et al. note at page 425 that since the A431 cell line and the many variants thereof have "a multitude of defects exemplified by its 78 chromosomes, it is clearly best to regard this cell line with caution when exploring the mechanism of action of EGF or in characterizing changes which relate in a meaningful way to neoplasia."

Gullick et al. in *Anal. Biochem.*, 141: 253–261 (1984) describe a radioimmunoassay for solubilized EGFr. Gullick et al. in the *Proc. R. Soc. Lond, B* 226: 127–134 (1985) report on the production of polyclonal and monoclonal antibodies to selected synthetic peptides from the EGFr.

Gullick et al. in *Cancer Res.*, 46: 285–292 (January 1986) describe the properties of two monoclonal antibodies produced to a synthetic peptide consisting of residues 985 to 996 from the cytoplasmic domain of EGFr. Further therein, samples of human tumors were solubilized in detergent and analyzed for the presence of functional EGFrs by autophosphorylation and immunoprecipitation using a monoclonal antibody "which binds to the native folded external domain of the human and rat EGF receptors".

Waterfield et al. [U.S. Pat. No. 4,933,294 filed Dec. 2, 1985 and issued Jun. 12, 1990, entitled "Method of Detecting Truncated Growth Factor Receptors"] disclose that neoplastic and other diseases can be diagnosed by assaying a human test sample, for example body fluid, tissue or cultured tumor explant calls, for structurally altered or abnormally expressed growth factor receptors. Claim 1 from which all the other claims therein depends reads "[a] method of diagnosis for the detection of abnormalities in mammalian cell growth comprising obtaining a test sample from a human and assaying the sample of a truncated epidermal growth factor receptor having at least a portion of its mature amino terminus deleted, and correlating detection of said truncated growth factor receptor with abnormal growth control in mammalian cells."

Waterfield et al.'s International Publication No. WO 85/03357 (published Aug. 1 1985) entitled "Improvements Relating to Growth Factors" is a foreign counterpart application to U.S. Pat. No. 4,933,294 (discussed immediately above). Claim 46 of that published application reads "[a] method of human diagnosis comprising assaying a human body fluid sample for EGF receptor." [That application was also published as European Patent Application No. 171,407 on Feb. 19, 1986.]

Cline et al. [U.S. Pat. No. 4,699,877 (filed Nov. 20, 1984 and issued Oct. 13, 1987)] describes methods and compositions for detecting the presence of tumors, wherein a physiological sample is assayed for the expression product of an oncogene.

Weber and Gill, *Science*, 224: 294 (1984), reported that human epidermoid carcinoma A431 cells in culture produce a soluble 105 kilodalton (kd) protein which they determined to be related to the cell surface domain of the EGFr. They further determined that the soluble receptor 105 kd protein was not derived from the membrane-bound intact receptor but was separately produced by the cell. [See also, Mayes and Waterfield, *EMBO J.*, 3: 531–537 (1984); and Cooper et al., *J. Virol.*, 48:752–764 (1983).]

Four years later, Weber in an abstract entitled "Truncated EGF receptor: functional aspects of its secretion," [*Acta Endocrino Logica*, 117 (Suppl. 287): 47 (No. 55) (1988)] reported that two products of the EGFr gene "are expressed in human A431 epidermoid carcinoma cells: the 'normal' 170 kDa receptor which is inserted into the membrane, and a 100 kDa EGF receptor-related protein (ERRP) which is secreted. . . ." That ERRP was described as corresponding to the extracellular domain of the EGFr. Weber further reported finding ERRP in another line of tumor cells, and that when solid A431 tumors were grown on athymic mice, that ERRP appeared in the blood of the mice and could be measured in the serum.

Co-pending U.S. patent application Ser. No. 389,920 (filed Aug. 4, 1989) discloses assays for detecting the external domain glycoprotein (gp 75) encoded by the c-erbB-2 oncogene or parts thereof in the body fluids of mammals. The application claims methods prognostic and diagnostic for neoplastic disease based upon such assays.

As indicated above, several methods have been used to detect EGFr levels in tumor tissues. There are, however, many cases in which tissue is not readily available or in which it is not desirable or not possible to withdraw tissue from tumors. Therefore, there is a need in the medical art for rapid, accurate diagnostic tests that are convenient and non-traumatic to patients. The invention disclosed herein meets said need by providing for non-invasive diagnostic/prognostic assays to detect and/or quantitate in mammalian body fluids, preferably serum, a portion of the EGFr which comprises substantially the ectodomain of EGFr.

SUMMARY OF THE INVENTION

Diagnostic/prognostic methods for neoplastic disease are provided, as well as, compositions and test kits for implementing such methods. The invention claimed herein is based upon the detection of a portion of the EGFr at elevated levels in the body fluids of mammals carrying a malignant tumor burden. Said portion of the EGFr comprises substantially the EGFr ectodomain. The inventors hereof show that one end of said EGFr portion has an amino acid sequence substantially identical to that reported for the N-terminus of the EGFr ectodomain [Ullrich et al., *Nature*, 309 (5967): 418–425 (May 31, 1984)]. Said EGFr portion, which is found in mammalian body fluids and has a molecular weight in the range of from about 90 kilodaltons (kd) to about 115 kilodaltons (kd), preferably in a range of from about 95 kd to about 105 kd, and more preferably in a range of about 100 kd, is herein termed "the EGFr ectodomain protein". Methods and compositions are provided for detecting and/or quantitating said EGFr ectodomain protein.

Further, diagnostic/prognostic methods are provided wherein fragments of said EGFr ectodomain protein are found in mammalian body fluids. For example, proteolytic activity in serum or in the kidney may break down the EGFr ectodomain protein into fragments. Thus, for example, in serum or in urine such fragments which contain one or more epitopes of said EGFr ectodomain protein may be detected and/or quantitated in the assays of this invention.

Representative methods and compositions according to this invention include those for identifying patients who have one or more malignant tumors. An exemplary method comprises the steps of detecting the level of the EGFr ectodomain protein as described herein in a sample of a patient's body fluid and determining whether that level is elevated above normal. As shown herein, malignant tumors release a higher level of said EGFr ectodomain protein into body fluids than do benign tumors or normal tissues. Thus, a higher than normal level of said EGFr ectodomain protein is indicative of the presence of one or more malignant tumors.

The invention provides for specific diagnostic/prognostic assays to detect and/or quantitate said EGFr ectodomain protein in the body fluids of mammals, and thereby detect tumors, quantitate their growth, and provide valuable information for the diagnosis and prognosis of neoplastic disease. An elevated level of said EGFr ectodomain protein in a host's body fluid, that is, above the normal background binding level, is indicative neoplastic disease.

Preferably, the mammal being tested is human, and the body fluid assayed is serum or plasma. An important parameter of the status and survival probability of a patient with neoplastic disease, such as breast, stomach including esophagus, colon, kidney, prostate, liver, urinary tract including bladder, lung, head and neck tumors and gynecologic cancers including ovarian, cervical, vaginal, endometrial and vulval cancers, can be determined by testing a body fluid, preferably serum or plasma, from the patient for the presence of said EGFr ectodomain protein at elevated levels.

The invention further provides for methods and compositions to detect and/or quantitate said EGFr ectodomain protein in mammalian tissue extracts. Preferably, the extracts are from the tissues listed in the paragraph immediately above as representative of neoplastic diseases that are preferred targets of the assays of this invention.

Exemplary means for detecting and/or quantitating said EGFr ectodomain protein, whether in mammalian body fluids or in tissue extracts include affinity chromatography, ligand binding assays, lectin binding assays and immunoassays, among other means. Immunoassays are a preferred means, most preferably a bridge immunoassay in a sandwich format. In such an immunoassay, antibodies reactive with epitope(s) on the EGFr ectodomain, preferably on said EGFr ectodomain protein can be used. Still further, in, for example, a competitive assay format, labeled proteins and/or polypeptides from the EGFr ectodomain, preferably on the EGFr ectodomain protein, can be used to detect and/or quantitate said EGFr ectodomain protein in mammalian body fluids and/or tissue extracts. Also, alternatively, as a replacement for said labeled proteins and/or polypeptides in such a representative competitive assay, labeled anti-idiotype antibodies that have been prepared against antibodies reactive with epitope(s) on the EGFr ectodomain, preferably on said EGFr ectodomain protein, can be used.

Also provided are compositions of matter comprising antibodies raised against said EGFr ectodomain protein containing an epitope or epitopes from said EGFr ectodomain protein, wherein said antibodies, either polyclonal or monoclonal or both, have specific binding affinity for epitope(s) on said EGFr ectodomain protein. Said antibodies are useful in assays according to this invention.

Further provided are compositions comprising said EGFr ectodomain protein and/or fragments thereof in a substantially pure form. Those compositions can comprise said EGFr ectodomain protein, preferably glycosylated or partially glycosylated, and/or glycosylated and/or partially glycosylated fragments thereof, that have been isolated from one or more mammalian body fluids, preferably from serum, or from one or more mammalian tissue extracts. Said substantially pure EGFr ectodomain protein and/or fragments thereof, can be useful serologically in detecting and/or quantitating said EGFr ectodomain protein in mammalian body fluids.

Further, this invention provides for assays to detect and/or quantitate antibodies to said EFGr ectodomain protein in the body fluids of mammals. Such assay results especially in correlation with the results of assays of this invention that determine the level of said EGFr ectodomain protein in the body fluids of a patient provide important information for diagnosing and monitoring the patient's condition, deciding upon a course of treatment and in making a prognosis.

Still further, the assay results of this invention in indicating the presence and/or level of said EGFr ectodomain protein in the body fluids of humans and/or the presence and/or level of antibodies to said EGFr ectodomain protein are prognostically and diagnostically useful in conjunction with data from assays of other markers for neoplastic disease, such as, hormone receptors, for example, estrogen receptors (ER) and progesterone receptors (PR).

Exemplary of the diagnostic and prognostic indications that may be provided by the methods of this invention are the correlations of the results of assays according to this invention and the following representative associations referenced in the Background above: elevated levels of intact EGFr in tissues have been found to correlate with both a decreased chance of long term survival as well as a shortened time to relapse and poor responsiveness to endocrine therapy in breast and endometrial cancers; also elevated levels of EGFr in tissues have been associated with good responsiveness of ovarian cancer to chemotherapy; also associated with such elevated levels of EGFr are squamous cell carcinomas of the cervix and lung and invasiveness of bladder tumors.

The assays of this invention are useful for detection of malignant disease both pre- and post-operatively. For example, patients displaying elevated levels of said EGFr ectodomain protein, even at relatively early stages of the disease, may, if the circumstances warrant, be treated more rigorously in order to increase their survival chances. Further, elevated levels of said EGFr ectodomain protein in a patient's body fluid, preferably serum or plasma, may indicate metastases requiring immediate intervention, for example, systemic chemotherapy or radiation therapy. Further, by monitoring for either increases or decreases in levels of said EGFr ectodomain protein in a patient's body fluid, the physician may be able to determine if a patient is responding to therapy or whether metastatic disease is present, stable or progressing. Still further, elevated levels of said EGFr ectodomain protein in a patient's body fluid may be used to detect and diagnose cancer including screening of populations for certain types of cancer.

The invention also provides for test kits that embody the assays of this invention wherein said test kits comprise antibodies reactive with said EGFr ectodomain protein. Further, said test kits can comprise labeled proteins and/or polypeptides from the EGFr ectodomain, preferably from said EGFr ectodomain protein, and/or labeled anti-idiotype antibodies prepared against antibodies that are reactive with said EGFr ectodomain protein. The assays can be solid phase assays but are not limited thereto, and can also be in a liquid phase format, and can be based on enzyme linked immunosorbent assays (ELISAs), particle assays, radiometric or fluorometric assays either unamplified or amplified, using, for example, avidin/biotin technology.

DETAILED DESCRIPTION OF THE INVENTION

The concept underlying the many facets of this invention is the discovery that cancer patients have in their body fluids elevated levels of a portion of the EGFr which has a molecular weight in the range of from about 90 kilodaltons (kd) to about 115 kd, preferably from about 95 kd to about 105 kd, and more preferably about 100 kd. That portion of the EGFr comprises substantially the EGFr ectodomain. The inventors hereof show that one end of the amino acid sequence of said EGFr portion is substantially identical to the amino acid sequence reported for the N-terminus of the EGFr [Ullrich et al., *Nature*, 309 (5967): 418–425 (May 31, 1984)]. As indicated above, said portion of the EGFr which is found in mammalian body fluids is herein termed "the EGFr ectodomain protein".

"Substantially" as used in the context of "substantially comprises the EGFr ectodomain" indicates that although said EGFr ectodomain protein found in mammalian body fluids may not comprise the identical amino acid sequence or may comprise more or less amino acids than that reported for the EGFr ectodomain, it is recognizable as comprising a significant portion of the EGFr ectodomain with an N-terminus substantially identical to that reported for the N-terminus of the EGFr and with a molecular weight in the ranges stated above. It can be appreciated that a protein extant within the body fluids would be subject to degradative processes, for example, proteolytic, among other processes; further, it can be appreciated that a protein produced by a neoplastic cell could be altered in sequence from that produced by a normal cell or by a cell in tissue culture. Thus, "the EGFr ectodomain protein" would encompass various species of the protein which may have different numbers of amino acids or different amino acids at some positions as well as different degrees of glycosylation from that reported for the EGFr ectodomain in the literature.

Amino acid sequence variations in such a naturally occurring protein include, without limitation, amino acid substitutions, extensions, deletions, truncations, interpolations and combinations thereof. Such variations fall within the contemplated scope of the invention provided the protein containing them has epitopes recognized by antibodies reactive with epitopes on EGFr ectodomain, preferably on the N-terminal 600 amino acids thereof. For example, the end to the EGFr ectodomain protein which is substantially identical in amino acid sequence to the N-terminus of the EGFr, may have a number of amino acids that differ from that reported in Ullrich et al., id., or several amino acids could be missing from the N-terminus; nevertheless, said protein would still be "substantially" the EGFr ectodomain protein according to this invention. The stated molecular weight ranges encompass such various species of the EGFr ectodomain protein, wherein the predominant species has a molecular weight of about 100 kd.

The finding that said EGFr ectodomain protein is in human serum and other body fluids has opened the way for the development of novel methods and compositions for the diagnosis, prognosis and treatment of neoplastic disease in humans and other mammals. The assays of this invention are both diagnostic and/or prognostic, i.e., diagnostic/prognostic. The term "diagnostic/prognostic" is herein defined to encompass the following processes either individually or cumulatively depending upon the clinical context: determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for neoplastic disease, diagnosing neoplastic disease, monitoring the disease status of patients with neoplastic disease, and/or prognosticating the course of neoplastic disease.

Assays herein are provided not only to detect and/or quantitate in the body fluids of mammals, preferably humans, said EGFr ectodomain protein but also antibodies to said EGFr protein. The assays of this invention provide important information concerning the disease status of the patient, and are useful for screening mammals for neoplastic disease, monitoring the progress of the disease, and for prognosticating the course of the disease and deciding upon appropriate treatment protocols.

Correlation of the results from the assays to detect and/or quantitate said EGFr ectodomain protein and antibodies reactive therewith, provides a preferred profile of the disease condition of a patient. For example, a patient may present with a large tumor, but the patient's level of said EGFr ectodomain protein may be relatively low. The lowness of the reading may be due to the patient's generation of antibodies to said EGFr ectodomain protein and not to the smallness of the tumor.

Further, correlation of the results of the assays of the invention with those for other markers for neoplastic disease, such as assays measuring the levels of estrogen receptors (ERs) and progesterone receptors (PRs) in breast cancer, for example, as outlined above in the Background, can still further enhance the diagnostic/prognostic profile of a cancer patient.

Assays for EGFr Ectodomain Protein in Mammalian Body Fluids

Non-invasive diagnostic/prognostic assays are provided to detect and/or quantitate said EGFr ectodomain protein in the body fluids of mammals, preferably humans. It can be appreciated that said EGFr ectodomain protein can be broken down in a patient's body fluids into various fragments, and that said fragments may be detected and/or quantitated by the assays of this invention if they contain one or more epitopes from the EGFr ectodomain protein that are recognized by the antibodies employed in this invention. For example, in a sandwich assay wherein two antibodies are used as a capture and a label antibody respectively, if both epitopes recognized by those antibodies are present on a fragment of said EGFr ectodomain protein, said fragment would be detected and/or quantitated according to such as immunoassay. Such fragments which are detected and/or quantitated according to methods of this invention are indicative of the presence of said EGFr ectodomain protein.

Such assays provide valuable means of monitoring the status of neoplastic diseases. In addition to improving prognostication, knowledge of the disease status allows the attending physician to select the most appropriate therapy for the individual patient. For example, patients with a high likelihood of relapse can be treated rigorously, usually involving systemic chemotherapy and/or radiation therapy. When there is a lesser likelihood of relapse, less aggressive therapies can be chosen. Because of the severe patient distress caused by the more aggressive therapy regimens, it would be desirable to distinguish with a high degree of certainty those patients requiring such aggressive therapies.

The present invention is useful for screening a wide variety of neoplastic diseases, including both solid tumors and hematopoietic cancers. Exemplary neoplastic diseases include carcinomas, such as adenocarcinomas and melanomas, and squamous cell carcinomas of the head and neck; mesodermal tumors, such as neuroblastomas and retinoblastomas; sarcomas, such as osteosarcomas, Ewing's sarcoma, and various leukemias; and lymphomas. Of particular interest are gynecologic cancers including ovarian, cervical, vaginal, endometrial and vulval cancers; gastrointestinal cancer, such as, stomach, colon and esophageal cancers; urinary tract cancer, such as, bladder and kidney cancers; skin cancer; liver cancer; prostate cancer; lung cancer; and breast cancer. Of still further particular interest are gynecologic cancers; breast cancer; urinary tract cancers, especially bladder cancer; lung cancer; gastrointestinal cancer, such as, stomach, colon and esophageal cancers; and liver cancer. Even further of particular interst are gynecologic cancers and breast cancer. Tumors which are known to overexpress intact EGFr may be good candidates for target neoplastic diseases for the assays of this invention, that is, such tumors may release into body fluids said EGFr ectodomain protein at elevated levels above normal. Particularly well studied are tumors of the breast and adenocarcinomas of the vulva which have been confirmed to overexpress EGFr. Preferably, in regard to tumors of the lung and cervix, squamous cell carcinomas have been particularly associated with elevated levels of EGFr. As outlined in the Background above, EGFr measurements have been determined to be markers for breast cancer and to provide valuable information diagnostically and prognostically, in correlation with other markers, such as, hormone receptor measurements, for example, with estrogen receptors (ERs) and progesterone receptors (PRs).

The body fluids that are of particular interest in assaying for said EGFr ectodomain protein according to the methods of this invention include blood, serum, semen, breast exudate, saliva, sputum, urine, cytosols, plasma, ascites, pleural effusions, amniotic fluid, bladder washes, bronchio-alveolar lavages, and cerebrospinal fluid. Blood, serum and plasma are preferred, and serum is the most preferred body fluid for screening according to the methods of this invention. The assays of this invention may also be useful in detecting and/or quantitating said EGFr ectodomain protein in tissue extracts.

From a knowledge of the structure of the external domain of the EGFr, a number of monoclonal or polyclonal antibodies can be generated that specifically recognize that protein. Because said EGFr ectodomain protein is found to exist freely in the biological fluids of mammals, it is possible to detect and/or quantitate the levels of that protein. Utilizing current antibody detection techniques that can quantitate the binding of monoclonal antibodies, made specifically to epitopes on the external domain of the EGFr, preferably to epitopes on the N-terminal 600 amino acids, one can determine the amount of said EGFr ectodomain protein in the fluids of cancer patients.

Such an assay can be used to detect tumors, quantitate their growth, and help in the diagnosis and prognosis of the human disease. The assays can also be used to detect the presence of cancer metastasis, as well as confirm the absence or removal of all tumor tissue following surgery, cancer chemotherapy and/or radiation therapy. It can further be used to monitor cancer chemotherapy and tumor reappearance. Representative immunoassays involve the use of monoclonal or polyclonal antibodies which can be appropriately labeled to detect and/or quantitate said EGFr ectodomain protein in the body fluids of mammals.

One preferred method involves, as a first step, obtaining a purified amount of the external domain of the EGFr (procedure detailed below) and using it as an immunogen to generate monoclonal antibodies in mice or other suitable hosts. Alternatively, in another preferred method, whole cells expressing intact EGFr on their membrane surface can be used as a source of antigen. Still further, in another preferred method, purified EGFr (for example, solubilized from membranes in an A431 lysate preparation and then purified as detailed below) is used as the immunogen. It is possible that numerous monoclonal antibodies could be generated to recognize different epitopes on said EGFr ectodomain protein, and such monoclonal antibodies can be used either singularly or in combination as a cocktail to increase the specificity and sensitivity of an assay.

It is preferred in a format where more than one antibody is used as, for example, in a sandwich format, in a competitive/sandwich format, or where a cocktail of antibodies are used, that the epitopes with which the antibodies are reactive be widely spaced. One representative and preferred assay of this invention comprises the use of three antibodies to epitopes that are sufficiently spatially removed from each other to produce effective results.

Besides using the intact EGFr, purified EGFr and/or whole external domain as an immunogen, fragments of said EGFr ectodomain protein, or protein/polypeptide generated by recombinant DNA means or otherwise biologically from said EGFr ectodomain protein, can be also used to generate specific monoclonal and/or polyclonal antibodies. Also, polypeptides corresponding to various sequences within the external domain sequence, preferably within the N-terminal 600 amino acids, small polypeptides (peptides) attached to an appropriate carrier protein, could be used as a source of immunogens. In all cases, the antibodies generated that are selected would have a specificity such that they have very limited cross-reactivity with other proteins present on the surface of both tumors and non-tumor cells. They would preferably not, for example, react with proteins which are present on the surface of many normal cells.

The diagnostic/prognostic assay itself would typically involve obtaining a small amount of body fluid, preferably serum, from the preferably human host. The presence of said EGFr ectodomain protein in the serum can then be detected and/or quantitated using a number of well-defined antibody diagnostic assays. Those can be Western blots, ELISAs (enzyme-linked immunosorbent assays), RIA assays (radioimmunoassay), competitive EIA or dual antibody sandwich assays, all commonly used in the diagnostic industry. In such immunoassays, the interpretation of the results is based on the assumption that the antibody or antibody combination will not cross-react with other proteins and protein fragments present in the serum that are unrelated to EGFr.

Below under the heading Bridge Immunoassay and in Example 2, details of a preferred format for the assays of this invention—a sandwich bridge immunoassay—are provided. Many other formats for detection and/or quantitation of said EGFr ectodomain protein according to this invention in body fluids are of course available, including, for example, conventional sandwich, competitive, and competitive/sandwich formats among others as indicated above.

Representative of one type of ELISA test is a format wherein a microtiter plate is coated with antibodies to EGFr extracellular domain, to purified EGFr and/or antibodies to whole cells expressing, preferably overexpressing EGFr, (that is, to intact EGFr wherein "intact" in this context indicates that the extracellular domain is expressed on the surface of cells), and to said microtiter plate is added a sample of a patient's serum. After a period of incubation permitting any antigen to bind to the antibodies, the plate is washed and another set of anti-EGFr extracellular domain antibodies and/or other antibodies that recognize epitopes on the EGFr ectodomain protein, which antibodies are linked to an enzyme, is added, incubated to allow a reaction to take place, and the plate is then rewashed. Thereafter, enzyme substrate is added to the microtiter plate and incubated for a period of time to allow the enzyme to work on the substrate, and the absorbance of the final preparation is measured. A large change in absorbance indicates a positive result.

It is also apparent to one skilled in the art of diagnostic/prognostic assays that antibodies to EGFr extracellular domain proteins and/or polypeptides can be used to detect and/or quantitate the presence of said EGFr ectodomain protein in the body fluids of patients. In one such embodiment, a competition immunoassay is used, wherein an EGFr extracellular domain protein/polypeptide is labeled, and a body fluid is added to compete the binding of the labeled EGFr extracellular domain protein/polypeptide to antibodies specific to the EGFr extracellular domain. Such an assay could be used to detect and/or quantitate said EGFr ectodomain protein.

Once antibodies having suitable specificity have been prepared, a wide variety of immunological assay methods are available for determining the formation of specific antibody-antigen complexes. Numerous competitive and non-competitive protein binding assays have been described in the scientific and patent literature, and a large number of such assays are commercially available. Exemplary immunoassays which are suitable for detecting a serum antigen include those described in U.S. Pat. Nos. 3,791,932; 3,817, 837; 3,839,153; 3,850,752; 3,850,578; 3,853,987; 3,867, 517; 3,879,262; 3,901,654; 3,935,074; 3,984,533; 3,996, 345; 4,034,074; and 4,098,876.

Antibodies employed in assays may be labeled or unlabeled. Unlabeled antibodies may be employed in agglutination; labeled antibodies may be employed in a wide variety of assays, employing a wide variety of labels.

Suitable detection means include the use of labels such as radionuclides, enzymes, fluorescers, chemiluminescers, enzyme substrates or co-factors, enzyme inhibitors, particles, dyes and the like. Such labeled reagents may be used in a variety of well known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233, 402.

Another means of detecting and/or quantitating said EGFr ectodomain protein may be the use of EGF affinity chromatography, for example as described in Buhrow et al., *J. Biol. Chem.*, 257: 4019–4022 (1982) as a ligand binding assay. A further means of detecting and/or quantitating said EGFr ectodomain protein be the use of lectin binding assays.

Bridge Immunoassay

A preferred assay for said EGFr ectodomain protein according to this invention is the bridge immunoassay format, which is described in detail in commonly owned, co-pending U.S. patent application Ser. No. 07/693,024 filed Feb. 28, 1991. That application is hereby specifically incorporated by reference. Briefly, the bridge immunoassay provides an immunoassay methodology wherein a universal capture system is employed, wherein an immunocomplex containing the sample analyte, the EGFr ectodomain protein, is formed in solution and then captured and insolubilized by a universal bridge receptor which links the immunocomplex to a solid phase through a first receptor thereto.

The bridge immunoassay provides a capture system comprising at least three receptors. The first receptor is bound to a solid phase and has as its ligand a second receptor or a ligand conjugated to said second receptor, wherein said second receptor is a bridge receptor, preferably an anti-hapten bridge receptor. The bridge receptor binds to a ligand conjugated to a sample analyte receptor, the third receptor. The third receptor has as its ligand either the analyte under assay or a further receptor which has as its ligand the analyte under assay.

The bridge immunoassay can be used in any standard immunoassay format including sandwich, competitive sandwich/competitive immunoassay formats. In a sandwich immunoassay format, a labeled fourth receptor, in this case to the sample analyte, is used to form a sandwich immunocomplex in solution with the analyte and the third receptor. After the initial liquid phase reaction when the immunocomplex sandwich is formed, the bridge receptor (second receptor) is added to the liquid sample where it binds to a ligand conjugated to the sample analyte receptor (third receptor) and pulls the immunocomplex out of solution by binding to the first receptor, which is bound to the solid phase. The amount of label (on the fourth receptor) that is immobilized upon the solid phase or remaining in the liquid phase can then be measured by conventional means to detect whether or not the analyte (said EGFr ectodomain protein in this invention) had been present in the sample and if so, determine the amount of analyte that had been present.

There are many different embodiments for the bridge immunoassay. A preferred embodiment to assay for the EGFr ectodomain protein of this invention is the bridge immunoassay in a sandwich format. In such a preferred bridge immunoassay format, the first receptor is preferably avidin or streptavidin, more preferably streptavidin [Zymed Laboratories, South S.F., Calif. (USA)] coated upon a solid phase, more preferably coated to the inner walls of polystyrene test tubes [most preferably, 12 mm ×75 mm; Nunc star tubes; Nunc, Napierville, Ill. (USA); catalog #470319] wherein the reaction volume is 0.5 mL and wherein 2.5 µg per tube of streptavidin was offered. In such a preferred assay, the second receptor (bridge receptor) is preferably a biotinylated bridge antibody, preferably a monoclonal antibody, which was raised to a hapten conjugated to an appropriate carrier protein, preferably fluorescein isothiocyanate (FITC) conjugated to KLH, preferably purified by HPLC. Said bridge receptor is at a concentration preferably of about 800 ng per tube. In such a preferred assay, the third receptor is an antibody, preferably a monoclonal antibody that recognizes an epitope on the ectodomain of the EGFr, preferably on the N-terminal 600 amino acids of the ectodomain, more preferably the monoclonal antibody, 31G7 (specified below), to which FITC is conjugated. The amount of said third receptor is preferably proportional to the amount of the bridge receptor (second receptor). It is preferred that there be about one to about 20 times more bridge antibody than third receptor (capture antibody), and still more preferred that there be about 4 to about 12 times more bridge antibody than third receptor on a molar basis. In such a preferred assay, the fourth receptor is an enzyme-labeled monoclonal antibody which recognizes an epitope on the ectodomain of the EGFr, preferably on the N-terminal 600 amino acids of the ectodomain, more preferably monoclonal antibody 4C7 (specified below); the enzymatic label on said fourth receptor is preferably horseradish peroxidase.

A preferred method of preparing the enzyme-labelled antibody for such an assay is the use of a heterobifunctional methodology of conjugation [Sullivan and Marks, *Methods in Enzymology:* (9) Methods for the Preparation of Enzyme-Antibody Conjugates for Use in Enzyme Immunoassay, 73:147 and ff. (1981)]. More specifically, it is preferred that the enzyme, preferably HRP, be thiolated using N-succinimidyl S-acetylthioacetate (SATA) as described in Duncan et al., *Anal. Biochem.*, 132: 68–73 (1983), and that it be coupled with an antibody activated by using one of the following three cross-linking reagents each of which is described in the article in brackets thereafter: succinimidyl 4-(N-maleimidomethyl) cyclohexane-1-carboxylate (SMCC) [Tsurata et al., *J. Histochem Cytochem.*, 33 (8) : 767 and ff. (1985)]; m - maleimidobenzoyl-N-hydroxysuccinimide ester (MBS) [Liu et al., *Biochem.*, 18 (4): 690 and ff. (1979)]; and N-succinimidyl bromoacetate (NSBA) [Bernatowicz and Matsueda, *Anal. Biochem.*, 155: 95–102 (1986)].

Example 2 below provides the details of a preferred protocol for a bridge immunoassay to detect and/or quantitate the EGFr ectodomain protein in the body fluids of mammals according to this invention.

Assays for Antibodies to the EGFr Ectodomain Protein

As indicated above, the level of antibodies to said EGFr ectodomain protein in a patient's body fluids is an important parameter in screening for neoplastic disease, monitoring, and prognosticating the course of the disease and on deciding upon a course of treatment. Such antibodies can be detected and/or quantitated by conventional means known in the art that are analogous to those means outlined above for detecting and quantitating said EGFr ectodomain protein according to this invention. A representative assay to detect and/or quantitate such antibodies is a competition assay in which a labeled EGFr extracellular domain protein/polypeptide, preferably from the N-terminal 600 amino acids, is precipitated by antibodies in patient serum in competition with a known quantity of monoclonal antibodies recognizing epitope(s) on the EGFr extracellular domain, preferably on the N-terminal 600 amino acids. One skilled in the art could adapt any of the formats outlined and referred to in the above section to detect and/or quantitate antibodies to said EGFr ectodomain protein. Further, the results of such assays for antibodies to the EGFr ectodomain protein can also be correlated with other indicators of neoplastic disease. For example, in the case of breast cancer, the results of the assays for said antibodies may be correlated with results of assays for hormone receptors, such as ERs and PRs.

Test Kits

The above outlined assays can be embodied in test kits to detect and/or quantitate said EGFr ectodomain protein in mammalian, preferably human, body fluids wherein such test kits can comprise antibodies, polyclonal and/or monoclonal, that recognize epitopes on said EGFr ectodomain protein made against, for example, purified EGFr, against purified EGFr extracellular domain, against EGFr extracellular domain proteins and/or polypeptides, and/or against whole cells expressing EGFr (that is, to intact EGFr). Such diagnostic/prognostic test kits can further comprise one or more other sets of antibodies, polyclonal and/or monoclonal, for a sandwich format wherein said other antibodies similarly recognize such epitopes on said EGFr ectodomain protein, and are appropriately labeled.

Test kits for an assay format wherein there is competition between a labeled EGFr extracellular domain protein/polypeptide and said EGFr ectodomain protein in the sample, for binding to an antibody, can comprise the combination of the labeled protein/polypeptide and the antibody in amounts which provide for optimum sensitivity and accuracy. Said antibody which recognizes appropriate epitopes can be either polyclonal and/or monoclonal.

Further, said test kits can comprise proteins and/or polypeptides from said EGFr ectodomain protein, alone or in combination with the aforementioned antibodies. Anti-idiotype antibodies to the anti-EGFr ectodomain antibodies, can be substituted for EGFr extracellular domain proteins and/or polypeptides in such test kits.

Abbreviations

The following abbreviations are used herein:

| AEV | avian erythroblastosis virus |
| ATCC | American Tissue Culture Collection |
| BSA | bovine serum albumin |
| °C. | degrees centigrade |
| cm | centimeter |
| DAB | diaminobenzidine tetrahydrochloride |
| DNS | 1,4-N,N- dimethyl amino-napthalene sulfonic acid |
| EDTA | ethylenediaminetetraacetic acid |
| EGF | epidermal growth factor |
| EGFr | epidermal growth factor receptor |

-continued

| EIA | enzyme immunoassay |
| ELISA | enzyme labeled immunosorbent assay |
| ER | estrogen receptor |
| ERRP | epidermal growth factor receptor-related protein |
| FITC | fluorescein isothiocyanate |
| fmol | femtomole |
| HEPES | 4-(2-hydroxyethyl)-1-piperazine ethane sulfonic acid |
| HPLC | high pressure liquid chromatography |
| hr | hour |
| HRP | horseradish peroxidase |
| IRMA | immunoradiometric assay |
| kd | kilodalton |
| KLH | keyhole limpet hemacyanin |
| L | liter |
| M | molar |
| mA | milliampere |
| MAb | monoclonal antibody |
| MBS | m-maleimidobenzoyl-N-hydroxysuccinimide ester |
| mg | milligram |
| min | minute |
| mL | milliliter |
| mM | millimolar |
| mm | millimeter |
| NFDM | non-fat dried milk |
| ng | nanogram |
| NHS | normal human serum |
| nm | nanometer |
| NP-40 | Nonidet P-40 (non-ionic detergent from Sigma Chemical Co. in St. Louis, MO) |
| NSBA | N-succinimidyl bromoacetate |
| PBS | phosphate-buffered saline |
| PEG | polyethylene glycol |
| PMSF | phenylmethylsulfonylfluoride |
| PR | progesterone receptor |
| RIA | radioimmunoassay |
| rpm | revolutions per minute |
| RPMI | Roswell Park Memorial Institute 1640 media |
| SATA | N-succinimidyl S-acetylthioacetate |
| S.D. | standard deviation |
| SDS | sodium dodecyl sulfate |
| SDS-PAGE | sodium dodecyl sulfate-polyacrylamide gel electrophoresis |
| sec | second |
| SMC | succinimidyl 4-(N-maleimidomethyl) cyclohexane-1-carboxytate |
| TGF-α | transforming growth factor-alpha |
| TMB | 3,3,5,5'- tetramethyl benzidine |
| TRIS | tris (hydroxymethyl) aminomethane or amino-2-hydroxymethyl-1,3-propanediol |
| TWEEN-20 | polyoxyethylene-sorbitan monolaurate (non-ionic detergent from Sigma Chem. Co., St. Louis, MO) |
| µg | microgram |
| µL | microliter |
| V | volt |
| vol | volume |
| xg | times gravity |

Specifically, the following one-letter codes are used to represent amino acids:

| A = alanine | M = methionine |
| C = cysteine | N = asparagine |
| D = aspartic acid | P = proline |
| E = glutamic acid | Q = glutamine |
| F = phenylalanine | R = arginine |
| G = glycine | S = serine |
| H = histidine | T = threonine |
| I = isoleucine | V = valine |
| K = lysine | Y = tyrosine |
| L = leucine | W = tryptophan |

Cell Lines

The following cell lines were used in the experiments herein described:

A431—Human epidermoid carcinoma cell line obtained from the ATCC, catalog #CRL 1555

SW620—Human colon adenocarcinoma cell line derived from a lymph node metastasis, obtained from the ATCC, catalog #CCL 227

SP2/0-Ag14—Non-secreting mouse myeloma cell line, obtained from the ATCC, catalog #CRL 1581

Preparations and Antibodies

The following preparations and antibodies were used in the examples below.

Preparation of A431 and SW620 Cell Lysates

A431 cell lysates were prepared from confluent cell monolayers grown in 54 T150 tissue culture flasks. The cells were rinsed twice with cold PBS with 1 mM PMSF (phenylmethylsulfonyl fluoride) (Sigma, St. Louis, Mo.) using approximately 10 mLs per wash. Five mLs of the wash solution were added to each flask, and the cells were removed with a cell scraper. The cells were pelleted and then resuspended into 15 mLs homogenization buffer (10 mM Tris-HCl, pH 7.4, 1.5 mM EDTA, and 1 mM PMSF) and disrupted with a Polyron homogenizer (Brinkman Instruments, Switzerland) using five 10-sec pulses at setting 4. The homogenate was pelleted in a Sorvall RC5C centrifuge [Du Pont Company, Wilmington, Del. (USA)] at 14,000 rpm for 15 min. The pellet was resuspended in 10 mL extraction buffer (50 mM Tris-HCl, pH 7.4, 150 mM NaCl, 1. mM EDTA, 1% TRITON X-100) [Sigma, St. Louis, Mo. (USA)], and 1 mM PMSF (Sigma Chem. Co.), mixed well and set on ice for 15 min. The extract was centrifuged in a Beckman microfuge 12 (Beckman Instruments, San Francisco, Calif.) for 15 min at high speed. The supernatant (lysate) was aliquoted and stored at −70° C.

Cell lysates from confluent monolayers of SW620 cells were also prepared as described for the A431 cells.

Preparation of Polyclonal Antibodies

The techniques for making polyclonal antibodies are conventional in the immunoassay art. Anti-peptide polyclonal antibodies are also made by conventional methods in the art as described in European Patent Publication No. 44,710 (published Jan. 27, 1982). Briefly, such anti-peptide antibodies are prepared by selecting a peptide from the EGFr amino acid sequence (Ullrich et al., supra), chemically synthesizing it, conjugating it to an appropriate immunogenic protein and injecting it into an appropriate animal, usually a rabbit or a mouse; then, either polyclonal or monoclonal antibodies are made, the latter by the Kohler-Milstein procedure.

Chemical synthesis of a peptide is conventional in the art and can be accomplished, for example, by the Merrifield solid phase-synthesis technique [Merrifield, *J. Am. Chem. Soc.*, 85:2149–2154 (963); Kent et al., *Synthetic Peptides in Biology and Medicine*, 29f.f., eds. Alitalo et al., (Elsevier Science Publishers 1985); and Haug, *ABL*, 40–47 (January/February 1987)].

Techniques of chemical peptide synthesis include using automatic peptide synthesizers employing commercially available protected amino acids; such synthesizers include, for example, Biosearch [San Rafael, Calif. (USA)] Models 9500 and 9600; Applied Biosystems Inc. [Foster City, Calif. (USA)] Model 430; MilliGen [a division of Millipore Corp.; Bedford, Mass. (USA)] Model 9050; and Du Pont's Ramp (Rapid Automated Multiple Peptide Synthesis) [DuPont Company, Wilmington, Del. (USA)].

All the polyclonal antibodies used for this invention were screened against purified EGFr, A431 cell lysates and SW620 lysates (from human colon adenocarcinima).

Preparation of Polyclonal Antibody EGFr #2

New Zealand white rabbits were immunized with 5 μg of purified EGFr derived from A431 cells as described below. The initial immunization consisted of the antigen emulsified, 1:1 (vol/vol) in Freund's complete antigen and injected into the popliteal lymph nodes. Subsequent boosts were given intraperitoneally at two week intervals, with the antigen emulsified in incomplete Freund's adjuvant. The animals were bled every two weeks by ear vein, and the sera assayed by ELISA against purified EGFr, against A431 cell lysates and against SW620 cell lysates. The procedure for those ELISAs is described within the preparation of the monoclonal antibodies below.

Preparation of Polyclonal Antibody PEP.EGFr #1

PEP-EGFr#1 polyclonal antiserum was made by immunizing New Zealand white rabbits with the peptide TBI 487 (a 20-mer at the C-terminal end of the EGFr cytoplasmic domain, amino acids 1167–1186, TAENAEYLRVAPQSSEFIGA) after conjugation to KLH with glutaraldehyde. The peptide was provided by Protein Chemistry, Triton Biosciences [Alameda, Calif. (USA)]. An immunization scheme similar to the one described above was used. For the initial immunization, 250 μg of peptide equivalent was used; subsequent boosts used 100 μg. The animals were bled, and the sera assayed as indicated above for polyclonal antibody EGFr #2.

Preparation of Polyclonal Antibody EGFr 421 π1

EGFr 421 #1 polyclonal antiserum was made by immunizing New Zealand white rabbits with the peptide TBI 421 (a 17-mer in the C-terminal region of the EGFr cytoplasmic domain, amino acids 984–1000, DVVDADEYLIPQQGFFS) after conjugation to KLH with glutaraldehyde. The peptide was provided by Protein Chemistry, Triton Biosciences [Alameda, Calif. (USA)]. The amounts of antigen used, and the immunization schedule were identical to that used to make PEP-EFGr #1. The animals were bled, and the sera assayed as indicated above for polyclonal antibody EGFr #2.

Preparation of Monoclonal Antibodies

Monoclonal antibodies useful in the present invention are obtained by well known processes as described in, for example, Gulfre and Milstein, "Preparation of Monoclonal Antibodies: Strategies and Procedures," in *Methods in Enzymology: Immunochemical Techniques*, 73:1–46 (Langone and Vanatis eds. Academic Press 1981); and in the classic reference, Milstein and Kohler, *Nature*, 256:495–497 (1975).

All the monoclonal antibodies used for this invention were screened against purified EGFr, A431 cell lysates and SW620 lysates.

MAbs 4C7, 26C3, 29C12 and 31G7

The monoclonal antibody 4C7 was made by fusing splenocytes from Balb/c mice immunized with A431 cells to the myeloma cell line SP2/0-Ag14 (ATCC CRL 1581 non-secreting mouse myeloma). Monoclonal antibodies 26C3, 29C12, and 31G7 were made by using to said myeloma cell line splenocytes from Balb/c mice immunized with EGFr purified from A431 cells.

Balb/c mice were immunized intraperitoneally with either $10^7$ A431 cells or 5 μg purified EGFr emulsified 1:1 (vol/vol) in RIBI adjuvant [RIBI ImmunoChem Research, Inc., Hamilton, Mont. (USA)]. The animals were boosted every two weeks with emulsified antigen. Sera were collected from the tail vein every two weeks and tested for reactivity in an ELISA assay (described below) against lysates of A431 and SW620 cells (ATCC CCL 227, human colon adenocarcinoma derived from a lymph node metastasis), as well as against purified EGFr. Animals with positive titers were boosted intravenously with antigen in PBS and sacrificed 4 days later for fusion. Splenocytes were fused with the SP2/0-Ag 14 cells at a ratio of 4:1 with a 50% polyethylene glycol 4000 solution [EM Sciences, Cherry Hill, N.J. (USA)] using the procedure of Kohler and Milstein [*Nature*, 256:495–497 (1975)]. Fused cells were gently washed and plated into 96-well plates at $2.5 \times 10^5$ splenocytes per well in RPMI. On days 1, 2, 3, 4, and 6 following fusion, half the media was removed and replaced with media supplemented with 0.1 mM hypoxanthine and 5.8 uM azaserine (Sigma, St. Louis, Mo.).

Supernatants were tested for reactivity in the ELISA assay on day 11. Vinyl assay plates (96-well) [Costar; Cambridge, Mass. (USA)] were coated with A431 lysate. (250 ng/well), SW620 lysate (250 ng/well), or purified EGFr (25 ng/well) overnight. After blocking with 4% non-fat dry milk, 0.05% TWEEN-20 in PBS for 1 hr at room temperature, 10 µL of supernatant was added to 50 µL PBS and allowed to incubate for 1 hr at 37° C. After washing in PBS with 0.05% TWEEN-20, the plates were incubated with 50 µL of rabbit anti-mouse IgG-horse radish peroxidase conjugate [Jackson ImmunoResearch, West Grove, Pa. (USA)] at a 1:3000 dilution in PBS for 30 min at 37° C. for 1 hr. Following the final wash, 50 µL of the TMB (3, 3', 5, 5' tetramethylbenzidine) substrate was added to the wells for a 15 min incubation. The color development was quenched by the addition of 50 µL 1 M phosphoric acid. The plates were read on a Molecular Devices Vmax kinetic microplate reader [Menlo Park, Calif. (USA)] at an optical density of 450 nm. Hybridomas were chosen that reacted positively on the A431 lysate and EGFr coated plates, yet negatively on the SW620 coated plates. All positive cell lines went through two cloning rounds by limiting dilution to ensure monoclonality.

Screening of Antibodies for Recognition of EGFr Ectodomain

EGFr ectodomain was purified from A431 tissue culture supernatant as described below. The antibodies were screened in an ELISA assay against the purified EGFr ectodomain as described below. Of the monoclonal antibodies to EGFr all but 29C12 recognized epitopes on the EGFr ectodomain.

RB Monoclonal 20B3.

The RB monoclonal 20B3 to which Example 1 below refers is a mouse monoclonal made to a peptide encoded by a retinoblastoma gene. The RB monoclonal is available from Triton Diagnostics Inc. [Alameda, Calif. (USA)].

MAb 225 [commercially available from Oncogene Sciences in Manhasset, N.Y. (USA)] recognizes an epitope in the binding site of the EGFr ectodomain. Its characterization is described in Masui et al., *Cancer Res.*, 44: 1002–1007 (1984).

EGFr Ectodomain Purification

As indicated above in the Background, Weber and Gill [*Science*, 224:294–297 (Apr. 20, 1984)] identified in the supernatant of A431 cells, a soluble 105-kilodalton protein which by the criteria of EGF binding, recognition by monoclonal and polyclonal antibodies to the EGFr, amino-terminal sequence analysis and carbohydrate content, is related to the cell surface domain of EGFr. Weber and Gill called that protein an "extracellular EGF receptor-related protein (ERRP)". A similar procedure herein was used to purify a protein of similar molecular weight (100–105 kd band) from the supernatant of A431 cells wherein said protein reacted with EGFr #2 (polyclonal antiserum made to EGFr purified from A431 cell membranes) in a Western blot, but was not recognized by the two polyclonal antisera (PEP-EGFr #1 and EGFr 421 #1) made to peptides respectively from the C-terminal end of EGFr and within the EGFr cytoplasmic domain.

The N-terminal 20 residues of that protein purified from the A431 supernatant was sequenced on automatic sequencing equipment (Applied Biosystems, Foster City, Calif.), and those residues were found to be identical to N-terminal residues described by Ullrich et al., supra for EGFr ectodomain. Thus, that protein purified from the supernatant of A431 cells is herein termed to be "purified EGFr ectodomain".

The procedure used to purify the EGFr ectodomain is as follows: A431 cells (ATCC CRL 1555, human epidermoid carcinoma cells derived from an 85-year-old human female) were grown to confluency, and supernatants were harvested from the tissue culture flasks and filtered through a 0.22 micron cellulose acetate filter to remove cell debris. The media was then concentrated ten-fold on a Minitan System: [Millipore Corp., Bedford, Mass. (USA)]. The media was applied to a 1.0×5 cm column packed with 5mL MAb 225-Sepharose affinity gel (wherein the Sepharose is available from sigma Chem. Co. and is linked to MAb 225 according to manufacturer's instructions). The column was loaded at a flow-rate of approximately 2 mL/min and then thoroughly washed with HTNG (20 mM HEPES, pH 7.5, 150 mM NaCl, 0.1% TRITON, 10% glycerol) buffer until a stable baseline absorbance at 280 nm as monitored on a Frac-100 fraction collector [Pharmacia, Piscataway, N.J. (USA)] was attained. Nonspecific binding was removed by washing the column with 1 M NaCl, followed by washing with HTNG until the baseline was attained. The EGFr ectodomain was eluted from the column with 10 column volumes of 50 mM triethylamine, pH 10.5. It was then washed with 20 column volumes of PBS containing 0.05% $NaN_3$ and stored. Fractions were monitored for the presence of the purified EGFr ectodomain by dotblot with $^{125}$I TGF-α. Those containing the purified EGFr ectodomain were dialyzed against HTNG buffer and concentrated in a Centriprep 30 [Amicon, Beverly, Mass. (USA)].

EGFr Purification Method

EGFr was solubilized from the membranes in an A431 lysate preparation by incubation in extraction buffer (10 mM HEPES, pH 7.5, 4 mM benzamidine, 3 mM EDTA, 0.5 units/mL aprotinin, 1% TRITON X-100, 10% glycerol, 100 mM NaCl, and 5 µg/mL leupeptin) [all chemicals available from Sigma, St. Louis, Mo.] for 15 min on ice. After centrifugation at 10,000×g for 10 min, the supernatant was collected, applied to a MAb 225-Sepharose column, and allowed to recirculate slowly overnight. The purification procedure of EGFr using immunoaffinity chromatography was identical, from this step on, to that described for the EGFr extracellular domain (above). Downward et al., *Nature*, 307:521–527 (1984) also describes a method for purifying EGFr.

ELISA Assay for Purified EGFr Ectodomain

Vinyl assay plates (96-well) [Costar, Cambridge, Mass. (USA)] were coated with 5 ng/well purified EGFr ectodomain diluted in PBS and incubated overnight at room temperature. The plates were blocked with 4% non-fat dry milk, 0.05% TWEEN-20 in PBS for 1 hr at room temperature followed by a wash in PBS, 0.5% TWEEN-20. Fifty µL of hybridoma supernatant were added to each well and allowed to incubate at 37° C. for 1 hr. After washing, the plates were incubated with 50 µL of rabbit anti-mouse IgG-horse radish peroxidase conjugate [Jackson ImmunoResearch, West Grove, Pa. (USA)] at a 1:3000 dilution in PBS for 30 min at 37° C. Following the final wash, the TMB (3,3',5,5' tetramethylbenzidine) substrate [Kirkegaard and Perry Laboratories, Inc., Gaithersburg, Md. (USA)] was added at 50 µg/well for 15 min. The color development was quenched by the addition of 50 µL of 1M phosphoric acid. Plates were read on a Vmax kinetic plate reader (Molecular Devices, Menlo Park, Pa.) at an optical density of 450 nm.

Tube Coating with Streptavidin

To Nunc star tubes (12 mm ×75 nm; Nunc catalog #470319) is added one-half mL of streptavidin in a coating buffer of sodium bicarbonate at pH 9.6 at a concentration of 5 µg of streptavidin per mL. The tubes are covered and stored at 2° C. to 8° C. for about 16 to 24 hours. The liquid is then aspirated from the tubes which are then washed twice with 2 mL of phosphate buffered saline and 0.05% TWEEN 20 wash buffer.

Two mL of PBS- 1% bovine serum albumin (BSA) blocking solution are added to the tubes which are then incubated at room temperature for about two to about four hours. The liquid is then aspirated from the tubes which are then washed twice with a 1% glucose solution. The liquid is then aspirated. The tubes are then uncovered and placed in a drying chamber until thoroughly dry, which occurs overnight. The dried tubes are then placed in heat-sealable Mylar (moisture-resistant plastic) pouch with a dessicant pack and maintained therein until ready for use in an assay according to this invention.

EGFr Ectodomain Protein/Polypeptide Production

As indicated above the complete amino acid sequence for the EGFr is known [Ullrich et al., *Nature*, supra]. EGFr extracellular proteins/polypeptides can be prepared recombinantly, synthetically or otherwise biologically. Exemplary of biologic means other than recombinant means to prepare a desired polypeptide or protein is to subject to selective proteolysis a longer EGFr extracellular polypeptide or protein containing the desired amino acid sequence. For example, said longer polypeptide or protein can be split with chemical reagents or with enzymes.

Synthetic formation of a polypeptide or protein requires chemically synthesizing the desired chain of amino acids by methods well known in the art, and discussed above under *Preparation of Polyclonal Antibodies*.

A "polypeptide" is defined herein to be a chain of amino acids covalently bound by peptide linkages composed of 50 or less amino acids. A "protein" is herein defined to be a chain of amino acids covalently bound by peptide linkages composed of more than 50 amino acids.

It is understood that, in some instances, amino acid sequence variations of naturally occurring proteins and polypeptides may be antigenic. Possible sequence variations include, without limitation, amino acid substitutions, extensions, deletions, truncations, interpolations and combinations thereof. Such variations are acceptable according to this invention provided the protein or polypeptide containing them is immunogenic and antibodies elicited by such a polypeptide or protein recognize epitopes on the naturally occurring EGFr ectodomain protein.

Further, it will be appreciated that the amino acid sequence of the EGFr extracellular domain can be modified by genetic techniques. One or more amino acids can be deleted or substituted. Such amino acid changes, especially if in a region which is not within an epitope of the polypeptide, may not cause any measurable change in the serological and/or immunogenic activity of a protein or polypeptide. The resulting protein or polypeptide will have substantially the same amino acid sequence and substantially the same biological activity.

The following examples are presented to help in the better understanding of the subject invention and for purposes of illustration only. They are not to be construed as limiting the invention in any manner.

EXAMPLE 1

Human Serum assayed in EGFr ELISA

Nunc certified polystyrene microtiter plates (Nunc Inter Med; Kamstrup, Denmark) were coated overnight at 4° C. with two EGFr monoclonals (29C12 and 4C7) and one negative control monoclonal (RB monoclonal 20B3) at 1 µg/well (100 µL) in PBS (10 mM sodium phosphate, pH 7.4, 0.1M NaCl). The coating solution was decanted, and the plates were blocked for 1.5 hours at room temperature with 200 µL 4% non-fat dried milk (NFDM) in PBS. The plates were decanted and then washed five times with wash buffer (PBS with 0.05% TWEEN-20, a non-ionic detergent from Sigma Chem. Co., St. Louis, Mo.).

A431 lysate was diluted in assay buffer (0.5% NFDM in PBS with 0.05% TWEEN-20) to yield standards ranging from 10 to 0.1 µg/mL of total protein. Normal human serum [NHS from Bioheme, Salt Lake City, Utah (USA)] was diluted 1:100 in assay buffer. The A431 lysate and NHS were added to the plates in duplicate (100 µL/well) and incubated for 1 hour at 37° C. The plates were then washed 5 times with the wash buffer.

Biotinylated monoclonal antibodies to EGFr—4C7, 26C3 and 31G7—were added to respective wells and incubated for 1 hour at 37° C. The plates were again washed 5 times and a goat anti-biotin horseradish peroxidase (HRP) conjugate [Zymed Laboratories, South San Francisco, Calif. (USA)] was added and incubated for 30 minutes at 37° C. The plates were washed and KPL [Kirkegaard and Perry Laboratories, Md. (USA)] 3, 3', 5, 5' tetramethylbenzidine (TMB) substrate was added, 100 µL/well, and allowed to develop for 10 minutes. The reaction was quenched using 100 µL 1M $H_3PO_4$. The plates were read with a spectrophotometer set at 450 nm (nanometers).

Reactivity of serum in the six different sandwiches formed was evaluated. The following are the six sandwiches wherein the asterisks indicate which antibody in the sandwich was labeled with biotin:

1. 29C12 (capture) and 4C7*;
2. 4C7 (capture) and 26C3*;
3. 4C7 (capture) and 31G7*;
4. RB 20B3 (capture) and 4C7*;
5. RB 20B3 (capture) and 26C3*; and
6. RB 20B3 (capture) and 31G7*.

The capture antibody (29C12) for the first sandwich was made to EGFr purified from A431 cell lysate; the capture antibody (4C7) for the second and third sandwich assays was made to intact EGFr (A431 cells); whereas the capture antibody for the last three sandwiches (RB20B3) was made to a peptide encoded by a retinoblastoma gene and was used as a negative control to test for any anti-mouse activity in the NHS.

The results indicated that there was EGFr activity in NHS in sandwiches 2 and 3 but not in 1 nor in the three negative controls (sandwiches 4–6). The capture antibody in sandwich 1 is 29C12 which is a monoclonal antibody that does not recognize epitopes on the ectodomain of the EGFr. Therefore, the results indicate that the portion of the EGFr that was captured in the assay contained at least part of the ectodomain of the EGFr.

EXAMPLE 2

Normal, Benign & Breast Cancer Serum Panel Test in EGFr Ectodomain Bridge Immunoassay A431 lysate (prepared according to the procedure detailed above) was diluted to yield calibrators with values ranging between 0.05–2 femtomole per milliliter (fmol/mL). Ten normal sera, ten benign breast sera (from Bioheme, Salt Lake City, Utah), and ten metastatic breast cancer sera [from Dr. Doug Tormey at the Clinical Center at the University of Wisconsin Center for Health Sciences at the Medical School, Department of Human Oncology, Madison, Wis. (USA)] were diluted 1:100 and 1:500 in assay buffer which comprised 50 mM TRIS, pH 7.4 with 1% BSA, 0.05% TWEEN-20, 0.01% DNS and 0.1% KATHON [5-chloro-2-methyl-4-isothiazolin-3-one and 2-methyl-4-isothiazolin-3-one; Rohm & Haas, Philadelphia, Pa. (USA)]. Two hundred µL of standard or diluted serum was added to Nunc star tubes coated with streptavidin by the coating procedure detailed above. Two hundred µL of a conjugate solution comprising the monoclonal antibody 31G7 conjugated to FITC at 500 ng/mL and the monoclonal antibody 4C7 labeled with HRP at 500 ng/mL in the assay buffer was then added to each tube, and the reaction was incubated for 2 hours at room temperature. Two hundred µL of a solution containing the biotinylated bridge receptor which is a mouse monoclonal raised against FITC (conjugated to KLH) in the assay buffer at 4 µg/mL was added to each tube and allowed to incubate 2 hours at room temperature. Tubes were decanted and washed three times with Tris/TWEEN-20 wash buffer (50 mM Tris at pH 7.4 and 0.05% TWEEN-20). One mL of TMB substrate was added to each tube and developed for 15 minutes at room temperature. The reaction was quenched with 1 mL 1M $H_3PO_4$. Tubes were read at 450 using a Chem-Stat tube reader [Ocean Scientific, Garden Grove, Calif. (USA)]. The concentration values for the captured EGFr ectodomain protein in fmol/mL were calculated for the serum samples using the A431 standard curve for which the values were calculated from the A431 calibrators using software accompanying the Chem-Stat tube reader.

As shown in Table 1 which tabulates the 1:500 values for the sera, which were within the range of the assay, at a cut-off of 0.9 fmol/mL, 60% of the cancer sera were positive and 0% of the normal and benign sera were positive. Further, as indicated at the bottom of Table 1, the mean for the cancer sera is 0.87 which is considerably higher than the means for the normal (mean is 0.38) and benign sera (mean is 0.59). Thus there is a higher concentration of the EGFr ectodomain protein captured in the bridge immunoassay by monoclonal antibodies, which recognize epitopes on the EGFr extracellular domain, in the cancer sera than in the normal and benign sera.

TABLE 1

| Normal Sera | | Benign Sera | | Cancer Sera | |
|---|---|---|---|---|---|
| Sample Nos. | fmol/mL | Sample Nos. | fmol/mL | Sample Nos. | fmol/mL |
| 89 | 0.04 | 1 | 0.44 | 1 | 0.68 |
| 90 | 0.55 | 2 | 0.18 | 2 | 0.94 |
| 91 | 0.54 | 3 | 0.87 | 3 | 0.80 |
| 92 | 0.08 | 4 | 0.56 | 4 | 0.94 |
| 93 | 0.53 | 5 | 0.54 | 5 | 0.92 |
| 94 | 0.12 | 6 | 0.77 | 6 | 0.53 |
| 95 | 0.40 | 7 | 0.41 | 7 | 1.16 |
| 96 | 0.54 | 9 | 0.64 | 8 | 0.90 |
| 97 | 0.46 | 10 | 0.77 | 9 | 1.04 |
| 98 | 0.11 | 11 | 0.70 | 10 | 0.82 |
| Mean | 0.38 | | 0.59 | | 0.87 |
| S.D. | 0.22 | | 0.21 | | 0.18 |

EXAMPLE 3

HPLC of Serum to Determine Approximate Size Range of EGFr Portions

HPLC was performed to determine the approximate size range for the proteins from sera captured by the monoclonal antibodies that recognize epitopes on the ectodomain of EGFr as indicated in the above two examples. Serum samples were run over a DuPont Zorbax Gf-250 sizing column [DuPont Chem. Co., Wilmington, Del. (USA)]. The mobile phase (buffer A) used was PBS (10 mM sodium phosphate at pH 7.4 with 0.1M NaCl) with 0.05% TWEEN-20. The serum samples were run in the following order: 1) normal mouse serum Sigma Chem. Co., St. Louis, Mo. (USA)] 2) normal human serum (from Bioheme) 3) metastatic breast cancer sera (from Dr. Tormey at The University of Wisconsin) and 4) normal mouse serum spiked with A431 lysate to yield a concentration of 62 fmol/mL. β-amylase (200,000), Albumin (66,000) and Carbonic Anhydrase (29,000) (markers from Sigma Chem., Co.) were run last as molecular weight standards. Two hundred µL of each sample was injected onto the column. The column was washed for 20 minutes with buffer A between sample applications. 0.5 mL fractions (30 seconds) were collected starting at exactly 3 minutes post-injection for all of the serum samples. The resulting fractions were diluted 1:1 in assay buffer and tested according to the sandwich bridge immunoassay described in Example 2.

No positive immunoassay results were found for the mouse serum. Activity was found in fractions 12 and 13 of the normal and cancer samples which correspond to a molecular weight range from about 70,000 kd to about 120,000 kd. No activity was found in any of the other fractions. In the A431-spiked normal mouse serum, positive assay results were found in fractions 11–15 corresponding to a molecular weight range from about 60,000 kd to about 200,000 kd. The results show that the positive EGFr activity found in serum is produced by a protein and/or proteins in a molecular weight range encompassing that for the ectodomain of the EGFr, approximately 100 kd. Further, the results show that the molecular weight range for the protein and/or proteins found in the A431-spiked normal mouse serum, encompasses that for the EGFr in its entirety, that is, about 170 kd.

EXAMPLE 4

Western Blotting of EGFr Ectodomain Protein from Human Serum

To characterize an antigen identified by an appropriate antibody, a modification of the Western blot as described by Towbin et al., *PNAS* (USA), 76:4350–4354 (1979) was used. Specifically, a 300 µL sample of normal human serum was reacted with an anti-EGFr polyclonal antibody, EGFR #2 at a 1:300 concentration in 900 μL PBS (10 mM sodium phosphate at 7.4 with 1M NaCl) overnight at 46° C. Immune complexes were precipitated by incubation with 75 μL of a 2% Protein A-Sepharose (Sigma Chem. Co.) suspension for 2 hr at 4° C. with end-over-end rotation. After being pelleted by centrifugation at 8,000 rpm for 5 min in a Beckman Microfuge 12 [Beckman Instruments, San Francisco, Calif. (USA)], the Protein A-Sepharose complexes were washed in one mL 100 mM NaCl, 10 mM Tris-HCl, pH 7.4, 0.2% NP-40 (Nonidet P-40; non-ionic detergent from Sigma Chem. Co., St. Louis, Mo.), followed by centrifugation. A subsequent wash was done using one mL 10 mM Tris-HCl, pH 7.4, 0.2% NP-40. After centrifugation, the immunoprecipitate was resuspended in 150 μL SDS-PAGE sample buffer (0.0625M Tris, pH 6.8, 3% SDS, 5% mercaptoethanol, 10% glycerol) and treated at 100° C. for 5 min to solubilize the immune complexes.

Proteins were analyzed by SDS-PAGE as described by Laemmli, *Nature*, 127:680–685 (1970). Samples were loaded onto a 7.5% Laemmli SDS-polyacrylamide gel and separated by electrophoresis at 8 milliampere (mA) for approximately 16 hrs. Separated proteins were transferred to a nitrocellulose filter [Schleicher and Schuell, Kane, N.H. (USA)] in a Trans-blot transfer cell [BioRad Laboratories, Hercules, Calif. (USA)] using a 20 mM Tris, pH 8.2, 125 mM glycine buffer with 20% methanol at 25 volt (V) for 16 hrs. After transfer was complete, the nitrocellulose filter was blocked by a one hr incubation in 4% non-fat dry milk in PBS with 0.05% TWEEN-20 to prevent non-specific binding.

The MAb 31G7 at 10 μg/mL in PBS-TWEEN-20 was reacted with the filter for 2 hrs at 37° C. After three 5-min washes in PBS-TWEEN-20, the filter was incubated in Vectastain goat anti-mouse (Vector Laboratories, Burlingame, Calif.) according to the manufacturer's directions, followed by incubation with the Vectastain ABC reagent (Vector Laboratories). A DAB [3, 3'-diaminobenzidine tetrahydrochloride (Sigma, St. Louis, Mo.) solution (10 mg in 50 mM Tris, pH 7.4, with 75 μL 30% $H_2O_2$) was used to visualize the reaction.

A broad band with a molecular weight of about 500,000 daltons (reported in the literature as the approximate molecular weight for the ectodomain of EGFr) was seen in the human serum sample. The Western blot of immunoprecipitated human serum was repeated on a larger volume (1.2 mL) of a different normal serum sample; again a broad band with a molecular weight of about 100,000 daltons was seen, yet in this case the band contained approximately four times the protein seen in the first Western blot.

EXAMPLE 5

Western Blotting to Determine Specificity

Identical samples of normal human serum were immunoprecipitated with either EGFr #2 polyclonal antiserum or PEP-EGFr #1 polyclonal antiserum using the methods described in Example 4. The immunoprecipitated proteins were separated by SDS-PAGE and then transferred to a nitrocellulose filter which was probed with the MAb 31G7. The 100 kd protein present in serum was successfully precipitated by EGFr #2 antiserum that recognizes epitopes along the entire EGFr molecule; however, it was not precipitated by PEP-EGFR #1 antiserum that recognizes only the C-terminal end of the cytoplasmic domain of the EGFr.

EXAMPLE 6

Purification of EGFr Ectodomain Protein from Human Serum

The EGFr ectodomain protein was purified from human serum in order to confirm its identity through amino acid sequence data on the 20 amino acids located at the N-terminus. An EGFr affinity column was made by coupling 12.8 mg of MAb 3G7 to 3 ml of tresyl-activated agarose [Pierce, Rockford, Ill. (USA)] according to the manufacturer's instructions. Prior to use, the column (1.0 cm by 20 cm) was washed with 10 column volumes each of: (1) 1M NaCl, (2) 50 mM triethylamine, pH 10.5, and (3) 50 mM sodium citrate, pH 3.0 to remove uncoupled antibody. The column was then equilibrated with 10 column volumes of 20 mM HEPES, pH 7.5 containing 150 mM NaCl, 0.1% Triton X-100 and 10% glycerol (HTNG buffer).

One liter of pooled normal human serum [Biomedical Resources, Hatboro, Pa. (USA); lot #BM0325501] was diluted 1:1 in 20 mM HEPES, pH 7.5 buffer, with 150mM NaCl and 0.1% Triton X-100 and filtered through a 0.45 micron filter. The serum was applied to the column at a flow rate of 30 ml per hour over a period of several days at 4° C. Before elution, the column was washed with 10 column volumes of: (1) HTNG buffer, (2) 1M NaCl, (3) distilled water, followed by (4) HTNG buffer. The EGFr ectodomain protein was eluted from the column in 5 column volumes of 50mM triethylamine, pH 10.5. Twenty-five fractions were collected (0.6 ml each).

All fractions were assayed at a 1:40 dilution in a bridge immunoassay essentially as described in Example 2. The only deviation from the protocol described in Example 2 was the use of the monoclonal antibody 4C7 labeled with HRP (using the NSBA cross-linking reagent rather than the SMCC cross-linking reagent) at 100 rather than 500 ng/mL. The concentration of EGFr ectodomain protein in fmol/ml was calculated in each fraction using a calibration curve. Fractions 3–25 were pooled and incubated with 1 ml Protein G-agarose [Genex Corporation; Gathersburg, Md. (USA)] for 1 hr to adsorb human IgG that may have been co-purified from the serum. The supernatant was then concentrated to approximately 500 μl in a Centricon 30 microconcentrator [Amicon, Danvets, Mass. (USA)].

The affinity-purified ectodomain protein was run on a 7.5% SDS-polyacrylamide reducing gel as described in Example 4. The proteins separated by electrophoresis were transferred to a ProBlott® membrane [Applied Biosystems, Foster City, Calif. (USA)] using the method recommended by the manufacturer. After transfer, the ProBlott membrane was stained for 30 sec in 0.1% Coomassie Blue R-250 in 40% methanol/1% acetic acid. A strongly staining band with a molecular weight of approximately 100,000 daltons (100 kd) was cut out of the membrane. The band was sequenced at the Protein Structure Laboratory, School of Medicine, University of California, Davis, Calif. (USA) by subjecting the band to direct solid-phase Edman degradation on a 470 gas-phase sequencer [Applied Biosystems; Foster City, Calif. (USA)]. The PTH amino acids were analyzed using an H-P 35900C high pressure liquid chromatograph [Hewlett-Packard Company; Palo Alto, Calif. (USA)].

The sequence for the 20 N-terminal amino acids was reported to be LEEKKVHQGTSNKLTQLGTF. The sequence was substantially identical to the N-terminal sequence of EGFr as reported in Ullrich et al., *Nature*, 309: 418–425 (1984), the only difference being that there was a histidine at position 7 at which position Ullrich et al. indicated a cysteine.

A portion of the ProBlott membrane was analyzed by Western blotting using the MAb 31G7 followed by the reagents in the Vectastain ABC kit [Vector Laboratories; Burlingame, Calif. (USA)] as described in Example 4. A diffuse band was visualized at the 100,000 dalton position, as was seen in the human serum samples in Example 4.

Various modifications of the invention in addition to those shown and described herein will become apparent to those in the art from the foregoing description. Such modifications are intended to be within the scope of the appended claims. The references cited herein are hereby incorporated by reference.

What we claim is:

1. A diagnostic/prognostic method for neoplastic disease comprising detecting and/or quantitating in a mammalian blood, plasma or serum sample a portion of the epidermal growth factor receptor (EGFr) which comprises substantially the EGFr ectodomain and which has a molecular weight in the range of from about 90 kilodaltons (kd) to about 115 kd, wherein an elevated concentration of said portion above the concentration for healthy mammals or for those with benign disease indicates the presence of neoplastic disease.

2. A diagnostic/prognostic method according to claim 1 wherein said molecular weight range is from about 95 kd to about 105 kd.

3. A diagnostic/prognostic method according to claim 1 where said molecular weight range is about 100 kd.

4. A diagnostic/prognostic method according to claim 1 wherein a lectin binding and/or ligand binding assay is used.

5. A diagnostic/prognostic method according to claim 4 wherein the human sample is serum.

6. A diagnostic/prognostic method according to claim 1 wherein an immunoassay and/or Western blot is used.

7. A diagnostic/prognostic method according claim 1 wherein a lectin binding and/or ligand binding assay is used.

8. A diagnostic/prognostic method according to claim 1 wherein the neoplastic disease is a cancer selected from the group consisting of lung cancer; gastrointestinal cancer selected from the group consisting of colon, stomach and esophageal cancer; and breast cancer.

9. A diagnostic/prognostic method according to claim 1 wherein the neoplastic disease is breast, colon or lung cancer.

10. A diagnostic/prognostic method according to claim 1 wherein the neoplastic disease is breast cancer, and the results of said method are correlated with the results of assays for estrogen receptors (ERs) and/or for progesterone receptors (PRs).

11. A diagnostic/prognostic method according to claim 1 which comprises the use of a bridge immunoassay format which is a sandwich assay wherein an immunocomplex is formed in a liquid reaction between said EGFr portion and antibodies reactive therewith, wherein one of said antibodies is conjugated to a hapten and one of which is enzymatically labeled, and wherein a biotinylated bridge antibody raised against said hapten is then added to the reaction mixture and links said immunocomplex to a solid phase that has been coated with avidin or streptavidin.

12. A diagnostic/prognostic method according to claim 11 wherein the antibodies are monoclonal, the hapten is fluorescein isothiocyanate (FITC), and the enzymatic label is horseradish peroxidase.

13. A diagnostic/prognostic method according to claim 1 which comprises the use of an ELISA assay or equivalent assay which can be unamplified or amplified using avidin/biotin technology.

14. A diagnostic/prognostic method according to claim 1 which comprises contacting a composition containing antibodies reactive with said EGFr portion with said mammalian sample and determining whether said antibodies bind to a protein in said sample.

15. A diagnostic/prognostic method according to claim 14 wherein a competitive immunoassay format is used, and wherein said composition further comprises labeled proteins and/or polypeptides from the EGFr ectodomain.

16. A diagnostic/prognostic method according to claim 14 wherein a competitive immunoassay format is used, and wherein said composition further comprises labeled anti-idiotype antibodies to antibodies reactive with epitopes on the EGFr ectodomain.

17. A diagnostic/prognostic method for detecting malignant tumor cells from a colon cancer, a lung cancer or a breast cancer in a patient which comprises:

a. contacting a blood, serum or plasma sample from said patient with a composition of antibodies having specificity for one or more epitopes within the EGFr ectodomain; and b. determining the amount of protein bound by the antibodies, wherein an elevated level of binding above the binding level for healthy humans or for those with benign disease indicates the presence of malignant tumor cells.

18. A method according to claim 1 wherein the sample is serum.

* * * * *

UNITED STATES PATENT AND TRADEMARK OFFICE
CERTIFICATE OF CORRECTION

PATENT NO. : 5,674,753
DATED : October 7, 1997
INVENTOR(S) : Jeanne P. Harvey, et. al.

It is certified that error appears in the above-identified patent and that said Letters Patent is hereby corrected as shown below:

Claim 18, line 43, "claim 1" should read — claim 17 —.

Signed and Sealed this

Second Day of June, 1998

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,674,753
DATED : October 7, 1997
INVENTOR(S) : Jeanne P. Harvey et al.

It is certified that error appears in the above-identified patent and that said Letters Patent is hereby corrected as shown below:

Column 27, Claim 4, line 24, "a lectin binding and/or ligand binding assay is used" should read — the mammalian sample is human —;

Claim 7, line 29, "according claim 1" should read — according to claim 1 —;

Column 28, Claim 18, line 43, "claim 1" should read — claim 17 —.

Signed and Sealed this

Twenty-fourth Day of November, 1998

Attest:

BRUCE LEHMAN

Attesting Officer

Commissioner of Patents and Trademarks